United States Patent [19]

Hernestam et al.

[11] Patent Number: 5,212,305
[45] Date of Patent: May 18, 1993

[54] PROCESS FOR PREPARING DELMOPINOL VIA THE INTERMEDIATES ISOXAZOLIDINES AND ISOXAZOLINES

[75] Inventors: Sven Hernestam, Malmö ; Bernt Thelin; Elisabeth Seifert, both of Lund; Arne Nilsson, Malmö, all of Sweden

[73] Assignee: Kabi Pharmacia Aktibolag, Sweden

[21] Appl. No.: 918,272

[22] Filed: Jul. 22, 1992

Related U.S. Application Data

[62] Division of Ser. No. 634,186, Feb. 19, 1991, Pat. No. 5,155,220.

[30] Foreign Application Priority Data

May 24, 1989 [SE] Sweden ............... 8901837-8
May 24, 1989 [SE] Sweden ............... 8901838-6

[51] Int. Cl.⁵ .......................... C07D 265/30
[52] U.S. Cl. .......................... 544/170
[58] Field of Search .......................... 544/170

[56] References Cited

U.S. PATENT DOCUMENTS 4,636,382 1/1987 Hernestam et al. ............... 544/170

*Primary Examiner*—Robert W. Ramsuer
*Attorney, Agent, or Firm*—Pravel, Hewitt, Kimball & Krieger

[57] ABSTRACT

The invention concerns a new process for preparing delmopinol using intermediates having the formula

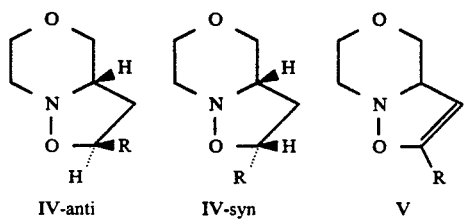

IV-anti    IV-syn    V wherein R is 2-propylpentyl optionally with one, two or three internal unsaturated bonds, or 2-substituted-2-propylpentyl optionally with one or two internal unsaturated bonds wherein the 2-substituent is a leaving group.

9 Claims, No Drawings

PROCESS FOR PREPARING DELMOPINOL VIA THE INTERMEDIATES ISOXAZOLIDINES AND ISOXAZOLINES

This is a division of application Ser. No. 07/634,186 filed Feb. 19, 1991 now U.S. Pat. No. 5,155,220.

The present invention concerns a new process for the preparation of delmopinol (recINN) as well as new intermediates used in the process.

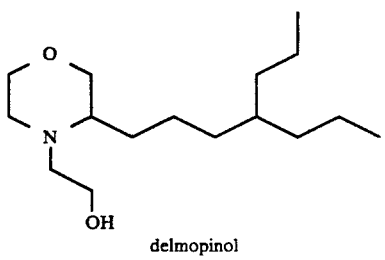
delmopinol

Delmopinol is a compound which has shown promising results as a plaque inhibitor. It is therefore intended to be used as an ingredient in e.g. mouthrinses and toothpastes. Delmopinol is a morpholino compound which is described in U.S. Pat. No. 4,636,382. This patent also describes several manufacturing methods that can be used for the preparation of this type of morpholino compounds. Up to now delmopinol has been prepared in large scale and in acceptable yields according to a process comprising 16 steps. It is obvious that this manufacturing process is both time and labour consuming. It is therefore an urgent need to provide a manufacturing process that is less time and labour consuming but still gives acceptable yields also in a large scale.

The present invention provides a solution to this problem.

SUMMARY OF THE INVENTION

According to the invention the intermediate isoxazolidines (IV) and isoxazolines (V) and delmopinol, 3-(4-propylheptyl)-4-morpholine-ethanol is prepared by a process comprising the following steps:

a) Preparation of mono- and polyunsaturated 4-propylheptyl compounds I and II, with a terminal olefinic or acetylenic bond.
   I: $CH_2=CH-R$
   II: $CH\equiv C-R$
   wherein R is 2-propylpentyl optionally having one, two or three internal unsaturated bonds, or 2-substituted-2-propylpentyl optionally having one or two internal unsaturated bonds, wherein the 2-substituent is a leaving group.

b) Reacting mono- and polyunsaturated 4-propylheptyl compounds (I and II) with morpholine nitrone (III)

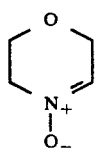

III to produce the compounds IV or V.

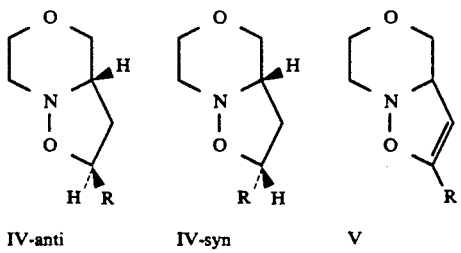

IV-anti    IV-syn    V

R is as defined for compounds I and II c) Reductive ringopening of the compounds IV and V to the compounds VIa, VIb and VIc having the formulas:

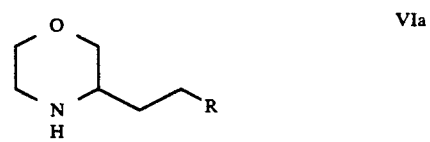

VIa

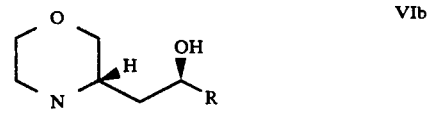

VIb

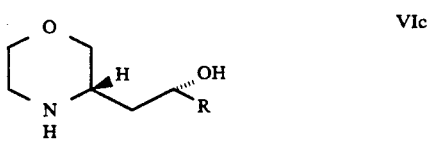

VIc d) Transferring VIb and VIc to the corresponding chloroanalogs.

e) Transferring the compounds of step d) to the compound VIa and f) Alkylating the compound VIa to 3-(4-propylpentyl)-morpholine-ethanol (delmopinol).

The mono- and polyunsaturated 4-propylheptyl compounds I and II are prepared according to examples 1-5.

The leaving group in step a) can be any of usual leaving groups and is suitable selected from hydroxy, alkoxy, acetoxy or tetrahydropyranyloxy.

The morpholine nitrone III, used in step b) can be prepared from N-hydroxylmorpholine by oxidation with e.g. yellow mercuric oxide, palladium and other oxidants, or from the same precursor by photochemical or electrochemical oxidation. It may also be prepared directly from morpholine by oxidation with 2-(phenylsulfonyl)-3-phenyloxaziridine or by catalytic oxidation using hydrogen peroxide and a catalyst, e.g. selenium dioxide or sodium tungstate.

The morpholine nitrone is too unstable to be isolated and is thus used directly for reaction with the unsaturated compounds I and II.

The compounds IV-anti and IV-syn (as racemates) are produced according to examples 6-12 in acceptable yields, and the unreacted starting material is easy to recover and recycle in the process. The compounds formed are diastereomers where IV-anti accounts for 90-98% and IV-syn for 2-10%. The stereo-chemistry of the adducts is based on analogy. See e.g. C. Hootelé et al., Bull. Soc. Chim. Belg., 1987, 96, 57 and references cited therein. The stereochemistry of compounds IV, as well as the degree of unsaturation, is not of importance in view of the total synthesis. All compounds IV converge to the same final product through the following steps.

Step c) can be carried out by treatment of compound IV and V, preferably with an acid e.g. p-toluenesulfonic acid, in a lower alcohol, preferably isopropanol, in a reductive milieu. This consists of a catalyst, preferably Pd-C, under $H_2$-pressure, preferably 3-7 atm.

Step d) is performed by reacting the reaction mixture from step c) with a chlorinating agent, preferably by boiling with thionyl chloride.

In step e) the compounds from step d) are dechlorinated by hydrogenation, preferably with Raney-Ni as catalyst.

In step f) finally, the compound VIa is alkylated, preferably by treatment with chloroethanol and potassium iodide and, at intervals, potassium hydroxide to give the desired 3-(4-propylheptyl)-4-morpholine-ethanol.

The most important aspect of this invention concerns the intermediates IV and V, as defined in the claims, and the preparation thereof, as these are key intermediates in the process for producing delmopinol.

The invention is further illustrated by the following

EXAMPLES

EXAMPLE 1

Preparation of 4-propyl-1-heptene (Ia)

To 100 g of 4-propylheptyl bromide in 400 ml of benzene was added 90 g of t-BuOK in 300 ml of DMSO. The temperature was kept below 50° C. during the addition. The mixture was stirred for 2 hrs and 600 ml of water was added. The organic phase was separated and the aqueous phase extracted with petroleumether (b.p. 40°-60°). The combined organic phases were washed with water and brine. After drying with $Na_2SO_4$ and evaporation the residue was distilled. Yield: 23.2 g (b.p. 56°-59° C. /75 Torr). $^1$H-NMR(CDCl$_3$): δ0.9(6H,CH$_3$), 1.2(9H,CH$_2$,CH), 2.0(2H,CH$_2$C=C), 4.8-5.1(2H,CH$_2$=C), 5.5-6.0(1H,CH=C)

EXAMPLE 2

Preparation of 4-propyl-1,3-heptadiene (Ib) and cis/trans-4-propyl-1,4-heptadiene (Ic)

To 80 g of PBr$_3$ in 250 ml of dry diethyl ether was slowly added 46 g of 4-hydroxy-4-propyl-1-heptene at −30° C. to −20° C. After the addition the temperature was kept at −25° C. to −10° C. another 2 hrs and then at +5° C. for 15 hrs. The reaction mixture was poured on ice (500 g) and diethyl ether (500 ml) was added. The ether phase was separated and washed with NaHCO$_3$-solution (2×250 ml), dried with MgSO$_4$ and evaporated. The residue (60.0 g) was taken up in 250 ml of benzene and 94 g of 1,8-diazabicyclo[5.4.0]undec-7-ene(1,5-5) and refluxed for 2 hrs. After cooling 1000 ml of diethyl ether was added and the ether solution washed with 5M HCl (2×300 ml) and water (3×250 ml), dried with MgSO$_4$ and evaporated. The residue (38.2 g) was distilled and the fraction 48°-56° C./8 Torr was 30.6 g. GC showed that it was composed of 47% of cis/trans-4-propyl-1,4-heptadiene (not separated) and 46% of 4-propyl-1,3-heptadiene. The 1,4- and 1,3-isomers were separated by preparative gas-liquid chromatography (Perkin Elmer F21) on a 12 m×8 mm column with 20% Carbowax 20M, 180° C. and 1.9 atm nitrogen pressure.

$^1$H-NMR(CDCl$_3$):
Ib: δ0.9(6H,CH$_3$), 1.3-1.5(4H,CH$_2$CC=C), 1.9-2.2(4H,CH$_2$C=C), 4.9-5.1(2H,CH$_2$=C), 5.8-5.9(1H,C=CHC=C), 6.5-6.7(1H,C=CCH=C)
Ic: δ0.8-0.9(6H,CH$_3$), 1.3-1.5(2H,CH$_2$CC=C), 1.9-2.1(4H,CH$_2$C=C), 2.6-2.8(2H,C=CCH$_2$C=C), 4.9-5.1(2H,CH$_2$=C), 5.1-5.3(1H,CH=C), 5.6-5.9(1H,CH=C)

EXAMPLE 3

Preparation of 4-hydroxy-4-propyl-1-heptene (Id)

113 g of 4-heptanone in 1000 ml of dry diethyl ether was slowly added to a solution of allylmagnesium bromide, prepared from 36.5 g of Mg and 178 g of allyl bromide in 500 ml dry diethyl ether. After the addition the mixture was refluxed for 10 hrs. The reaction mixture was poured on a mixture of 150 g ice, 450 ml of 20% NH$_4$Cl and 350 ml of 5M HCl. The ether phase was separated and the water phase extracted with diethyl ether (3×100 ml). The combined organic phases were then washed with a Na$_2$CO$_3$-solution and water, dried with Na$_2$SO$_4$ and evaporated. The residue was distilled. Yield: 142 g (b.p. 38°-40° C./0.1 torr)

$^1$H-NMR(CDCl$_3$): δ0.9(6H,CH$_3$), 1.3-1.6(9H,CH$_2$,OH), 2.1-2.3 (CH$_2$C=C), 5.0-5.2(CH$_2$=C), 5.6-6.1(CH=C)

EXAMPLE 4

Preparation of 2-propylpentyl tosylate

To a mixture of 52 g 2-propylpentanol and 86 g of p-toluenesulfonic acid in 175 ml of chloroform was added at 0°-3° C. and under N$_2$-atmosphere 48 g of pyridine. The mixture was kept at 0° C. for 30 minutes and at room temperature for 19 hrs. After cooling the reaction mixture, 3M HCl (300 ml) was added. The organic phase was separated and washed with water and brine. Drying with Na$_2$SO$_4$ and evaporation gives 110 g of 2-propylpentyl tosylate.

$^1$H-NMR(CDCl$_3$): δ0.8(6H,CH$_3$), 1.1-1.8(9,CH$_2$,CH), 2.4(3H,ArCH$_3$), 3.9(2H,OCH$_2$), 7.2-7.9(4H,ArH)

EXAMPLE 5

Preparation of 4-propyl-1-heptyne (IIa)

18.4 g of lithium acetylide ethylenediamine complex was charged in an argon-flushed flask. DMSO was then added (100 ml) and the mixture cooled to 15° C. 50 g of 2-propylpentyl p-toluenesulfonate was slowly added. After the addition the mixture was stirred at room temperature for 1 hr and then 50 ml of water was added carefully with vigorous stirring (the temperature was kept below 35° C.). The mixture was poured into 600 ml of water and extracted with hexane (3×100 ml). The combined hexane phases were washed with brine and dried with Na$_2$SO$_4$. The hexane was distilled off and the residue distilled at reduced pressure. Yield 13.1 g (b.p 75°-80° C./85 Torr).

$^1$H-NMR(CDCl$_3$): δ0.9(6H,CH$_3$), 1.3(9H,CH$_2$,CH), 1.9(1H,CH≡C), 2.2(2H,CH$_2$C≡C)

EXAMPLE 6

General procedure for preparation of isoxazolidines (IV) and isoxazoline (V) (method A)

To a mixture of the terminal alkene/alkyne (10 g), morpholine (19 g) and $Na_2WO_4,2H_2O$ (2.7 g) in methanol (50 g) and ethanol (50 g) was added 35% $H_2O_2$ (43 g) at a rate to keep the temperature at 50°-60° C. Additional ethanol (100 ml) was added and the mixture kept at 50°-60° C. for 18 hrs. Most of the methanol/ethanol was evaporated in vacuo whereupon water (300 ml) was added and the mixture extracted with diethyl ether (4×50 ml). The organic phase was washed with water and brine. Drying with $Na_2SO_4$ and evaporation gives the isoxazolidines(IV)/isoxazoline(V).

(Other combinations of solvents are possible e.g. with $CHCl_3$, toluene and $CH_3CCl_3$.)

EXAMPLE 7

Preparation of isoxazolidine IVd (method A)

70 g of 35% $H_2O_2$ was added to a mixture of 31 g of morpholine, 125 ml of methanol, 125 ml of ethanol, 19 g of 4-hydroxy-4-propyl-1-heptene and 4.8 g of $Na_2WO_4,2H_2O$ at a rate to keep the temperature at 50°-80° C. An additional amount of 200 ml of ethanol was added and the mixture was kept at 50°-60° C. for 18 hrs. Most of the methanol/ethanol was evaporated in good vacuum, whereupon 600 ml of water was added and the mixture was extracted with ether (4×200 ml). The ether phase was treated with 5M HCl (4×100 ml) and 13.5 g of the starting material was recovered. The acidic aqueous phase was alkalized and extracted with ether. Drying with $Na_2SO_4$ and evaporation gave 5.9 g of IVd (90% anti + 10% syn).

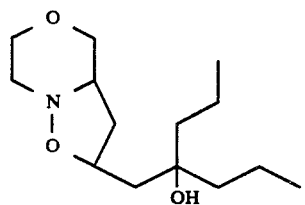

IVd

EXAMPLE 8

Preparation of isoxazolidine IVd (method B)

735 g of 30% $H_2O_2$ was added to 330 g of morpholine and 52 g of $Na_2WO_4,2H_2O$ in 400 ml of water, slowly under cooling. The temperature of the reaction mixture was kept below 20° C. One half of this nitrone mixture was then added to a refluxing mixture of 100 g of 4-hydroxy-4-propyl-1-heptene and 900 ml of methanol. After the addition refluxing was continued for 2.5 hrs whereupon the second half of the nitrone mixture was added and refluxing continued for another 2.5 hrs. After cooling the mixture was extracted with toluene (750 ml). The toluene mixture was extracted with 5M HCl (650 ml). From the organic phase 57 g of starting material, 4-hydroxy-4-propyl-1-heptene, was recovered. The aqueous phase was adjusted to pH 8.8 with 5M NaOH and extracted with toluene (500 ml). After drying with $Na_2SO_4$ and evaporation 37 g of IVd was recovered as syn-anti mixture.

EXAMPLES 9-12

Further examples 9-12 were prepared persuant to the process described in Example 6. These are presented in table I.

In Example 12 the product (Va) has not been isolated in pure form. Yield has been determined by $^1$H-NMR ($CDCl_3$): δ0.9(6H,$CH_3$), 1.3(9H,$CH_2$,CH), 4.5(1H,CH=C). The product can be used as intermediate in subsequent reactions without giving any by-products.

TABLE I

| Example | Unsaturated compound | | Product | | Yield (%)[1] | Ratio syn/anti[2] |
|---|---|---|---|---|---|---|
| 9 | | Ia | | IVa | 10 | 3:97 |
| 10 | | Ib | | IVb | 60 | 10:90 |
| 11 | | Ic | | IVc | 24 | 3:97[3] |

TABLE I-continued

| Example | Unsaturated compound | | Product | Yield (%)[1] | Ratio syn/anti[2] |
|---|---|---|---|---|---|
| 12 | | IIa | Va | 12 | — |

[1] Yields are not optimized.
[2] The stereochemistry of the adduct is based on analogy. See e.g C. Nootelé et al., Bull. Soc. Chim. Belg., 1987, 96, 57 and references cited therein.
[3] Compound IVc are formed as a 50:50 mixture of cis- and trans-isomers, where the syn-anti ratio of each is approx. 3:97.

EXAMPLE 13

Reductive ringopening of isoxazolidine IVd

A mixture of 10 g of isoxazolidine IVd, 27 g of p-toluene-sulfonic acid and 1.5 g of 10% Pd-C in 100 ml of isopropanol was shaken in a Parr bottle at 70°–80° C. and 3–7 atm of $H_2$ for 15 hrs. After cooling, the reaction mixture was filtered and the isopropanol was evaporated in a good vacuum. An excess of 5M NaOH was added and the mixture was extracted with diethyl ether. After drying and evaporation 8.8 g of a mixture of VIa, VIb and VIc (R=2-propylpentyl) was recovered.

EXAMPLE 14

Chlorination of hydroxyalkyl morpholines VIb and VIc (R=2-propylpentyl) and subsequent dechlorination 15 ml of thionyl chloride was added to 5.0 g of a mixture of compounds VIa, VIb and VIc (R=2-propylpentyl) in 7 ml of chloroform and the mixture was stirred at 20° C. for 3 hrs and refluxed for 1 hr. After evaporation 5M NaOH (25 ml) was added and the mixture was extracted with diethyl ether (3×15 ml). The combined ether phases were washed with water and brine. Drying and evaporation gave 4.8 g of the chloroanalogs and VIa.

This mixture, together with 5 g of Raney-Ni catalyst, 5 g of triethylamine and 250 ml of dioxane, was hydrogenated at 100° C. and 120 atm of $H_2$ for 24 hrs. The reaction mixture was filtered through Celite and evaporated. 30 ml of 5M NaOH was added and the mixture extracted with diethyl ether (3×15 ml). After drying and evaporation 4.3 g of pure 3-(4-propylheptyl)morpholine was recovered.

EXAMPLE 15

Preparation of 3-(4-propylheptyl)-4-morpholine-ethanol

A mixture of 2.5 g of 3-(4-propylheptyl)morpholine, 3.5 g of chloroethanol, 1.1 g of potassium iodide and 7 ml of ethanol was refluxed for 5 hrs. Then 0.3 g of KOH in 1.5 ml of ethanol was added and refluxing continued for 2 hrs when another 0.2 g of KOH in 1.0 ml of ethanol was added. Refluxing for 7 hrs was followed by a third addition of 0.1 g of KOH in 0.5 ml of ethanol. After another 2 hrs of refluxing the solvent was evaporated and 10 ml of water was added. The mixture was extracted with diethyl ether (3×10 ml) and the combined organic phases were washed with brine. After drying and evaporation 2.5 g of 3-(4-propylheptyl)-4-morpholine-ethanol was recovered.

We claim:

1. A process for preparing 3-(4-propylpentyl)-morpholine-ethanol (delmopinol) comprising:

a) reacting a mono- or polyunsaturated 4-propylheptyl compound having the formula I or II:
   I. $CH_2=CH-R$  II. $CH\equiv C-R$
   wherein R is:
   2-propylpentyl optionally with one, two or three internal unsaturated bonds; or
   2-substituted-2-propylpentyl optionally having one or two internal unsaturated bonds wherein the 2-substituent is a leaving group with a morpholine nitrone (III)

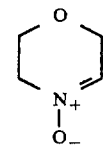

to produce the compounds of the formula:

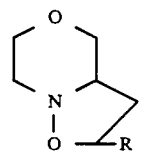

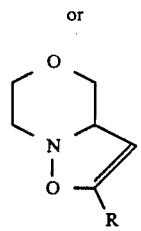

b) reductive ring opening of compounds IV or V to compounds of the formulas:

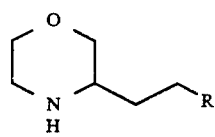

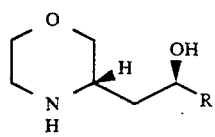

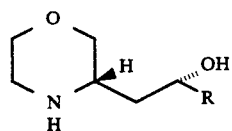

VIc c) reacting the mixture of VIb and VIc with a chlorinating agent;
d) dechlorinating the compounds of step c) to the compound VIa by hydrogenating; and
e) alkylating the compound VIa to render delmopinol.

2. The process according to claim 1 wherein the leaving group of the 2-substituted-2-propypentyl is selected from hydroxy, alkoxy, acetoxy or tetrahydropyranyloxy.

3. The process according to claim 1 wherein R of formula I is 2-propylpentyl, 2-propyl-1-pentenyl, 2-propyl-2-pentenyl or 2-hydroxy-2-propylpentyl.

4. The process according to claim 1 wherein R of formula II is 2-propylpentyl.

5. The process according to claim 1 wherein the compound IV is s diastereomer of:

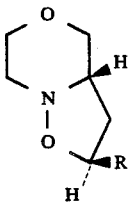 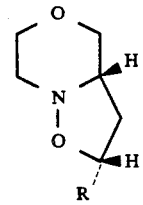

IV-anti    IV-syn

6. The process according to claim 5 wherein the compound IV comprises from about 90 to about 98% of IV-anti and from about 2 to about 10% of IV-syn.

7. The process according to claim 1 wherein step b) comprises treating compounds IV and V in a reductive media with an acid in the presence of an alkanol.

8. The process according to claim 1 wherein the compounds of step d) are hydrogenated in the presence of Raney nickel.

9. The process according to claim 1 wherein the compound VIa in step e) is treated with chloroethanol, potassium iodide and potassium hydroxide.

* * * * *